(12) United States Patent
Clark et al.

(10) Patent No.: US 6,723,302 B1
(45) Date of Patent: Apr. 20, 2004

(54) MODEL FOR CELL MIGRATION AND USE THEREOF

(75) Inventors: Richard A. Clark, Poquott, NY (US); Doris Greiling, Deal (GB)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 09/300,104

(22) Filed: Apr. 27, 1999

Related U.S. Application Data (62) Division of application No. 08/723,789, filed on Sep. 30, 1996, now Pat. No. 5,935,850.

(51) Int. Cl.$^7$ .......................... A61K 49/00; C12Q 1/00; C12Q 1/02; G01N 33/567; C12M 1/34
(52) U.S. Cl. .......................... 424/9.1; 435/4; 435/7.21; 435/29; 435/284.1; 435/287.1
(58) Field of Search .............................. 435/7.21, 4, 29, 435/13, 284.1, 287.1, 7.1, 325, 395; 424/9.1, 422, 423, 424; 800/3

(56) References Cited

U.S. PATENT DOCUMENTS 5,866,167 A * 2/1999 Van Bossuyt ................ 424/520
5,916,758 A * 6/1999 Hurle et al. .................. 435/7.8

FOREIGN PATENT DOCUMENTS

EP            0157359      *   9/1985   .......... A61K/37/12

OTHER PUBLICATIONS

Knox et al. Journal of Cell Biology. 102: 2318–2323, Jun. 1986.*
Brown et al. American J of Pathology. 142(1): 273–283, Jan. 1993.*
Ciano et al. Laboratory Investigation. 54(1): 62–70, 1986.*
Houdebine, Production of pharmaceutical proteins from transgenic animals, 1994, Journal of Biotechnology, Vol 34, pp. 269–287.*
Kappel et al., Regulations gene expression in transgenic animals, 1992, Current Opinion in Biotechnology, vol. 3, pp. 548–553.*
Ciano et al., Laboratory Investigation 54(1):62–70 (1986).
Knox et al., J Cellular Physiology 132:501–508 (1987).
Knox et al., J Cell Biology 102:2318–2323 (Jun. 1986).
Nicosia et al., Am J Pathology 145(5):1023–1029 (Nov. 1994).
Nicosia et al., Am J Pathology 128(1):78–90 (Jul. 1987).
Tomasek and Akiyama, Anatomical Record 234:153–160 (1992).
Schor et al., J Cell Science 109:2581–2590 (1996).
Middelkoop et al., Cell Tissue Res 280:447–453 (1995).
Kartha and Toback, J Clin Invest 90:288–292 (1992).
Bartold and Raben, J Periodont Res 31:205–216 (1996).
Bell et al., Proc Natl Acad Sci USA 76(3):1274–1278 (Mar. 1979).
Brown et al., Am J Pathology 142(1):273–283 (Jan. 1993).
Polarek, et al., Wounds, 6(2):46–53 (1994).

* cited by examiner

*Primary Examiner*—Shin-Lin Chen
(74) *Attorney, Agent, or Firm*—Rogalsky & Weyand, LLP (57) ABSTRACT

The invention provides the development of models for cell migration, including an in vitro model and an in vivo model. The in vitro model for cell migration comprises a first extracellular matrix containing a cell (the cell which will migrate) and a second extracellular matrix in physical contact with the first extracellular matrix. The first extracellular matrix simulates a first natural environment in which the cell naturally resides, and the second extracellular matrix simulates a second natural environment into which the cell naturally migrates from the first natural environment. The in vivo model according to the subject invention comprises an animal model having a naturally occurring first extracellular matrix containing a cell, and a second extracellular matrix in physical contact with the first extracellular matrix. The first and second extracellular matrices are generally as described above for the in vitro model, except that the first extracellular matrix is part of an animal model. The primary uses of the models are for screening substances for their effect on cell migration, and for screening extracellular matrices for their effect on cell migration.

23 Claims, 1 Drawing Sheet

FIG. 1

SEQUENCE LISTING

<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:synthesized
      peptide which includes RGD sequence of human
      fibronectin

<400> SEQUENCE: 1

Gly Arg Gly Asp Ser Pro
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:synthetic
      control peptide

<400> SEQUENCE: 2

Gly Arg Gly Glu Ser Pro
 1               5

MODEL FOR CELL MIGRATION AND USE THEREOF

This application is a divisional of U.S. Ser. No. 08/723,789, filed Sep. 30, 1996, now allowed U.S. Pat. No. 5,935,850.

The subject matter of this application was made with support from the United States Government under National Institutes of Health Grant Nos. AG 10143 and AR 42987.

FIELD OF INVENTION

The subject invention is directed to models for cell migration, and more particularly to in vitro and in vivo models which are especially useful for studying fibroblast cell migration during wound healing.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

After injury, a fibrin-rich clot fills the wound as a result of the local extravasation of plasma (Clark 1993b). This fibrin-rich provisional matrix, which also contains other matrix components like fibronectin (FN) and vitronectin as well as fibrin (Clark et al. 1981), forms a scaffold for the inward migration of the cells involved in early wound repair (Clark 1993a; Clark 1993b; Clark et al. 1982a; Clark 1996; Clark et al. 1996). Concomitantly, platelets release a plethora of growth factors, some of which bind to the fibrin meshwork. Subsequently, blood leukocytes, especially neutrophils and monocytes, migrate into the fibrin-rich provisional matrix. The neutrophils phagocytize and kill contaminating microorganisms (Tonnesen et al. 1988), while the monocytes mature into growth factor-producing macrophages (Shaw et al. 1990). Fibrin undergoes intermolecular crosslinking by formation of $\epsilon$-($\gamma$-glutamyl)lysine [$\epsilon$-($\gamma$-glu)lys] isopeptide bonds in the presence of plasma transglutaminase (Pisano et al. 1968). Crosslinking of $\gamma$ chains within fibrils forms dimers while intermolecular crosslinking among $\alpha$ chains creates oligomers and larger chain polymers (Mosesson et al. 1989; Shainoff et al. 1991). More recent in vitro studies indicate that in addition to $\gamma$ dimers, higher order forms of crosslinked $\gamma$ chain multimers form slowly and progressively over a period of hours to days (Siebenlist and Mosesson 1992). Coagulation factor XIIIa stabilizes the structure of the provisional matrix by cross-linking fibrin homocomplexes (Lorand 1972), and fibrin and FN heterocomplexes (Mosher 1975; Mosher 1976). FN is probably an important part of the invasion process in vivo since it is able to bind to cells and to other extracellular matrix (ECM) proteins simultaneously, and since fibroblasts can use FN as a substrate for migration in vitro (Hsieh and Chen 1983). Simultaneous with clot evolution during the first three days after injury, fibroblasts and endothelial cells in the underlying subcutaneous tissue proliferate (Clark 1993b). Fibroblasts and endothelial cells appear most numerous along the edge and base of the wound, with lesser numbers further away. By the third day after injury increased numbers of fibroblasts greatly expand the subcutaneous fibrous septae coursing between the fat lobules beneath the wound, and envelop individual adipocytes in proximity to the wound as well. Nevertheless, no fibroblast invasion of the wound clot is observed. Endothelial cells within blood vessels adjacent to the wound proliferate, causing marked vessel hypertrophy but do not move into the wound space (Clark et al. 1982b; Clark et al. 1982c).

Three days after injury, fibroblasts expressing abundant provisional matrix integrins (Xu and Clark 1996) migrate from the collagenous matrix of the dermis into the wound matrix as part of granulation tissue formation. Presumably this transmigration is in response to platelet-derived growth factor (PDGF) (Seppa et al. 1982; Senior et al. 1983) and other growth factors released by platelets and monocytes (Shimokado et al. 1985; Ross et al. 1986; Rappolee et al. 1988). Although PDGF is a potent mitogen and chemoattractant for fibroblasts (Seppa et al. 1982; Ross and Raines 1990), the full set of functional requirements for fibroblast transmigration from one matrix into another have not been defined.

Due to the complexity of the in vivo situation, three different in vitro models have been used in the past to study fibroblast invasion of a fibrin clot. Graham et al. (Graham et al. 1984) embedded explants of chick flexor tendons in a fibrin matrix and studied the migration, proliferation, and collagen synthesis of the fibroblasts. Migration in this system was induced by fetal bovine serum (FBS) but not by physiological concentrations of platelet lysate or PDGF. Brown and his coworkers (Brown et al. 1993) overlaid fibroblasts attached to tissue culture dishes with a thin fibrin layer and observed that cells migrated into the fibrin within 24 hours. This migration process was dependent on the nature of the fibrin clot: cross-linking of the fibrin $\alpha$-chains by factor XIIIa enhanced the number of invading cells. Knox et al. observed that the presence of FN (Knox et al. 1986) and plasminogen and its activators (Knox et al. 1987) were necessary for fibroblast invasion of a plasma clot on which the fibroblasts were seeded.

Before invasion of the fibrin clot, however, and in contrast to these in vitro models, resident tissue fibroblasts in normal dermis are surrounded by a matrix mainly composed of type I collagen. An often used in vitro model for the dermis is a relaxed hydrated collagen gel with embedded fibroblasts which acquire the dermal phenotypic characteristics of resident dermal fibroblasts (Elsdale and Bard 1972; Bell et al. 1979; Grinnell 1994). Just as in vivo, there is a low level of cell proliferation (Sarber et al. 1981) and collagen biosynthesis (Mauch et al. 1988), but an increased release of collagenase (Nusgens.et al. 19814; Unemori and Werb 1986). Furthermore, fibroblasts in relaxed collagen gels are less responsive to growth factors (Nakagawa et al. 1989; Nishiyama et al. 1990). An explanation for the different behavior of cells in the collagen gel in comparison to tissue culture plastic is that different kinds of extracellular matrix can dramatically affect cell functions and behavior by regulating gene expression and second messenger pathways (Hay 1991; Clark et al. 1995; Streuli et al. 1995; Tremble et al. 1995; Xu and Clark 1996). For example, when fibroblasts are cultured in collagen gels, $\alpha2$ integrin gene expression is increased (Klein et al. 1991; Xu and Clark 1996) and the autophosphorylation of PDGF-receptor is decreased (Lin and Grinnell 1993).

Integrins are a family of cell surface receptors which are primarily responsible for cell adhesion (Hynes 1992). All integrins are composed of one $\alpha$ and one $\beta$ subunit. A large number of integrins are responsible for the interaction of fibroblasts with the proteins of the provisional matrix. The integrins $\alpha3\beta1$, $\alpha4\beta1$, $\alpha5\beta1$ and $\alpha v\beta3$ mediate adhesion of adult human dermal fibroblasts to FN (Elices et al. 1991; Gailit et al. 1993; Gailit and Clark 1996). $\alpha v\beta3$ is the only known fibroblast integrin that recognizes fibrinogen (Smith et al. 1990; Gailit and Clark 1996). When wound fibroblasts migrate into the fibrin/FN-rich clot, α3β1 and α5β1 fibronectin receptors, but not α2β1 collagen receptors, are dramatically up-regulated (Xu and Clark 1996). α2β1 collagen receptors increase on wound fibroblasts later at day 7 when collagen accumulates in the wound area (Welch et al. 1990; Clark et al. 1995).

A need continues to exist for an understanding of the regulation of interactions between cells and extracellular matrix and the functional mechanisms involved during wound repair.

SUMMARY OF THE INVENTION

This need is met by the development of models for cell migration, including an in vitro model and an in vivo model, according to the subject invention. The in vitro model for cell migration comprises a first extracellular matrix containing a cell (the cell which will migrate) and a second extracellular matrix in physical contact with the first extracellular matrix. The first extracellular matrix simulates a first natural environment in which the cell naturally resides, and the second extracellular matrix simulates a second natural environment into which the cell naturally migrates from the first natural environment.

The in vivo model according to the subject invention comprises an animal model having a naturally occurring first extracellular matrix containing a cell, and a second extracellular matrix in physical contact with the first extracellular matrix. The first and second extracellular matrices are generally as described above for the in vitro model, except that the first extracellular matrix is part of an animal model.

Having thus described the in vitro and in vivo models according to the subject invention, uses of the models are numerous. The primary uses are for screening substances for their effect on cell migration, and for screening extracellular matrices for their effect on cell migration.

In one particular embodiment, the invention provides a defined, easily modulated, reproducible in vitro model which simulates the transmigration process from a homeostatic collagenous extracellular matrix into a provisional extracellular matrix environment that resembles early cutaneous wounds. The dermal equivalent was supplied by fibroblasts embedded in a three-dimensional relaxed collagen gel (Bell et al. 1979). The dermal equivalent was attached to a fibrin-fibril coated dish and surrounded by a freshly-formed fibrin gel. The transmigration of fibroblasts from the opaque collagen gel into the transparent fibrin gel could be quantified visually by counting the cells in the fibrin gel under an inverted microscope. This system allowed the study of the interactions between migrating cells, growth factors, and the physiological extracellular matrices present in this model of an early wound and the definition of the involved mechanisms and integrins. Fibroblast invasion of the fibrin gel was stimulated by platelet releasate, a natural mixture of growth factors, and by recombinant PDGF-BB, a cytokine found in vivo in the early phase of wound repair (Clark 1996). The migration was dependent on the presence of plasminogen. FN had to be present in both the collagenous and the provisional extracellular matrix to allow the transmigration process. Furthermore, the process was inhibited by RGD peptide and appeared to be mediated by α5β1 integrins.

BRIEF DESCRIPTION OF THE DRAWING

These and other features and advantages of this invention will be evident from the following detailed description of preferred embodiments when read in conjunction with the accompanying drawing in which.

DETAILED DESCRIPTION OF THE INVENTION

As used herein, a matrix is an interdigitating polymer bundle. Extracellular matrices include, for example, collagen, fibrin, fibronectin, and hyaluronic acid. Artificial extracellular matrices are biocompatible and include, for example, dextran polymers, polyvinyl chlorides, polyglycolic acids, polylactic acids, polylactic coglycolic acids, and silicon. A description of artificial (or synthetic) extracellular matrices is provided in Putnam and Mooney (1996).

As further used herein, a "substance" is a biological response modifier. Examples of such biological response modifiers include, but are not limited to, chemotactic factors, growth factors, cytokines, autocoids, and prostanoids.

The subject invention provides a model for cell migration. Cell migration occurs in many natural situations. For example, during wound repair fibroblasts migrate from a collagenous stroma extracellular matrix into a fibrin extracellular matrix. As another example, tumor cells migrate within a host, for example from a collagen extracellular matrix into a basement membrane extracellular matrix or from an epidermal (basement membrane) extracellular matrix into a collagen extracellular matrix. Cells also migrate during tissue morphogenesis. Cells migrate through a basal lamina, as when white blood cells migrate across the vascular basal lamina into tissues in response to infection or injury, or when cancer cells migrate from their site of origin to distant organs via the bloodstream or lymphatic vessels, a process known as metastasis.

The purpose of the subject invention is to provide a model for such cell migration. In one embodiment, the model of the subject invention is an in vitro model. In a further embodiment, the model is an in vivo model.

The in vitro model for cell migration comprises a first extracellular matrix containing a cell (the cell which will migrate) and a second extracellular matrix in physical contact with the first extracellular matrix. The cell can be any suitable cell, such as a fibroblast (e.g. a dermal skin fibroblast or a subcutaneous skin fibroblast), an endothelial cell, a monocyte/macrophage, or a tumor cell.

The first extracellular matrix simulates a first natural environment in which the cell naturally resides, and the second extracellular matrix simulates a second natural environment into which the cell naturally migrates from the first natural environment. For example, in wound repair the migrating cell may be a skin fibroblast and its first natural environment is collagenous stroma. The skin fibroblast, during wound repair, naturally migrates from the collagenous stroma into a fibrin clot which fills the wound. Thus, the first natural environment of the skin fibroblast is the collagenous stroma and the second natural environment of the skin fibroblast is the fibrin clot. The first extracellular matrix of the in vitro model is chosen to simulate the collagenous stroma with the skin fibroblasts therein. For example, the first extracellular matrix can be a contracted collagen gel produced according to the methods described in Example II. The second extracellular matrix of the in vitro model is chosen to simulate the fibrin clot. For example, the second extracellular matrix can be a fibrin gel, also produced according to the methods described in Example II, or an artificial extracellular matrix. It may also be useful to provide other components in the first and/or second extracellular matrix, such as fibronectin or hyaluronic acid.

The in vitro model according to the subject invention can be produced by any means known in the art. For example, the model can be two dimensional by providing the second extracellular matrix coated onto a surface (such as a microtiter plate, a petri dish, etc.), with the first extracellular matrix which includes the cells physically positioned on the second extracellular matrix. The cells from the first extracellular matrix will "outmigrate" over the surface of the second extracellular matrix. Alternatively, the model can be three dimensional by surrounding the first extracellular matrix with the second extracellular matrix (see FIG. 1 where the fibrin extracellular matrix is cast as a gel around the collagen gel extracellular matrix). The cells from the first extracellular matrix will "transmigrate" into the second extracellular matrix.

The migration of cells can be monitored or studied using the in vitro model. It should be readily apparent to those skilled in the art that the migration of cells can only be monitored or studied if the cells are detectable. This can be accomplished several ways. In one embodiment which includes a fibrin gel into which the cells migrate, the fibrin gel is transparent and the cells can be visualized with a light microscope. Alternatively, the cells provided in the first extracellular matrix can be labeled with a detectable marker. Such detectable markers are known in the art, and include, for example, radioactive labels, fluorescent labels, vital dyes (these non-toxic dyes stain living cells), and labels added by molecular manipulation (such as the βgal gene). The movement of the labeled cells from the first extracellular matrix to the second extracellular matrix can thus be monitored.

The subject invention also provides an in vivo model. The in vivo model according to the subject invention comprises an animal model having a naturally occurring first extracellular matrix containing a cell, and a second extracellular matrix in physical contact with the first extracellular matrix. The cell and first and second extracellular matrices are generally as described above for the in vitro model, except that the first extracellular matrix is part of an animal model. For example, a full thickness skin wound is made in an animal (such as a Yorkshire or Minipig). The collagenous stroma of the animal is the first extracellular matrix of the in vivo model, and the second extracellular matrix is provided as a fibrin gel or some artificial extracellular matrix. It may also be desirable with the in vivo model to provide additional cells (like the cells present in the first extracellular matrix of the animal or cells that are intrinsically different from the cells naturally residing in the animal) between the first extracellular matrix and the second extracellular matrix. Then, the migration of those additional cells can also be monitored to determine cell migration into the second extracellular matrix.

Having thus described the in vitro and in vivo models according to the subject invention, uses of the models are numerous. The primary uses are for screening substances for their effect on cell migration, and for screening extracellular matrices for their effect on cell migration. Accordingly, the subject invention also provides a method of screening substances for the effect of such substances on cell migration. The method comprises: providing an in vitro model for cell migration as described above; determining a rate of first migration of the cells from the first extracellular matrix into the second extracellular matrix; adding a substance to the in vitro model; and determining a rate of second migration of the cells from the first extracellular matrix into the second extracellular matrix after addition of the substance, wherein an increase in rate of first migration to rate of second migration indicates that the substance increases cell migration, and wherein a decrease in rate of first migration to rate of second migration indicates that the substance decreases cell migration. As indicated above, the cell migration being monitored can be outmigration (in a two dimensional format where the second extracellular matrix is coated on a surface) or transmigration (in a three dimensional format where the second extracellular matrix is cast as a gel, for example, around the first extracellular matrix). Having initially screened the substance for effect on cell migration using the in vitro model, the substance can then be further screened by providing an in vivo model for cell migration as described above, determining a rate of first migration of the cells from the first extracellular matrix into the second extracellular matrix in the in vivo model; adding the substance to the in vivo model; and determining a rate of second migration of the cells from the first extracellular matrix into the second extracellular matrix after addition of the substance to the in vivo model, wherein an increase in rate of first migration to rate of second migration indicates that the substance increases cell migration, and wherein a decrease in rate of first migration to rate of second migration indicates that the substance decreases cell migration in said in vivo model. The use of the in vitro and in vivo models together to screen substances thus provides two levels of screening. As indicated above, it may be desirable when using the in vivo model to provide a plurality of the cells positioned between the first extracellular matrix and the second extracellular matrix of the in vivo model. The method would then further comprise determining another rate of first migration of the plurality of cells from between the first extracellular matrix and the second extracellular matrix into the second extracellular matrix in the in vivo model; and determining another rate of second migration of the plurality of cells from between the first extracellular matrix and the second extracellular matrix into the second extracellular matrix after addition of the substance to the in vivo model, wherein an increase in another rate of first migration to another rate of second migration indicates that the substance increases cell migration, and wherein a decrease in another rate of first migration to another rate of second migration indicates that the substance decreases cell migration in said in vivo model. These additional cells provide an additional means for determining migration of cells into the second extracellular matrix, especially useful when the amount of cells present in the naturally occurring first extracellular matrix are limited or not as easily detected. The additional cells can readily be labeled before they are positioned between the first and second extracellular matrices, and thus can be readily detected. Alternatively, additional cells can be added that are intrinsically different from cells naturally residing in the animal, and detectable based on that difference.

The in vivo model as described above can also be used without the in vitro model to itself screen for substances that affect cell migration. Such a method comprises providing an in vivo model for cell migration as described above, determining a rate of first migration of the cells from the first extracellular matrix into the second extracellular matrix in the in vivo model; adding a substance to the in vivo model; and determining a rate of second migration of the cells from the first extracellular matrix into the second extracellular matrix after addition of the substance to the in vivo model, wherein an increase in rate of first migration to rate of second migration indicates that the substance increases cell migration, and wherein a decrease in rate of first migration to rate of second migration indicates that the substance decreases cell migration in the in vivo model.

The invention also provides for preliminary screening which comprises providing a cell and a first and second extracellular matrix, and determining that the cell can move on the first extracellular matrix and the second extracellular matrix. This preliminary screen can precede the screening of substances and/or extracellular matrices (see below) with the in vitro or in vivo models, as a means of determining that the cells in question can move on the chosen extracellular matrix. If the cells cannot move on the chosen extracellular matrix, then cell migration will not occur and the method of screening for substances or extracellular matrices that affect cell migration would be meaningless.

The invention further provides a method of screening extracellular matrices for the effect of such extracellular matrices on cell migration. The method comprises providing an in vitro model for cell migration as described above; determining a rate of first migration of the cells from the first extracellular matrix into the second extracellular matrix; substituting an artificial extracellular matrix for the second extracellular matrix in the in vitro model; and determining a rate of second migration of the cells from the first extracellular matrix into the artificial extracellular matrix, wherein an increase in rate of first migration to rate of second migration indicates that the artificial extracellular matrix increases cell migration, and wherein a decrease in rate of first migration to rate of second migration indicates that the artificial extracellular matrix decreases cell migration. Preferably, the second extracellular matrix is a fibrin gel when the model is being used to study wound repair.

As with the method of screening substances, the method of screening extracellular matrices can also utilize the in vivo model. Such a method comprises providing an in vivo model for cell migration as described above (again, with the second extracellular matrix preferably being a fibrin gel when the model is being used to study wound repair); determining a rate of first migration of the cells from the first extracellular matrix into the second extracellular matrix; substituting an artificial extracellular matrix for the second extracellular matrix in the in vivo model; and determining a rate of second migration of the cells from the first extracellular matrix into the artificial extracellular matrix, wherein an increase in rate of first migration to rate of second migration indicates that the artificial extracellular matrix increases cell migration, and wherein a decrease in rate of first migration to rate of second migration indicates that the artificial extracellular matrix decreases cell migration.

EXAMPLE I

In Vivo Model
Porcine Cutaneous Wound Models

Full-thickness skin wounds. Full-thickness excisional wounds were made by an 8 mm circular punch into the paravertebral skin of Yorkshire or Minipigs; dressed with Tegaderm™, a polyurethane occlusive dressing; and harvested 1 to 10 days later as previously described (Welch et al. 1990).

Reinjury model (primed wounds). For reinjured wounds, full-thickness wounds were made as described above; however, on the 5th or 7th day after wounding, granulation tissue was completely removed by curettage. These wounds were harvested 1–3 days later.

Fresh wounds with exogenous material. For wounds receiving exogenous material, full-thickness wounds were made as described above and blotted free of blood. To each wound space, 150 µl of 3 mg/ml fibrinogen (New York Blood Center, New York, N.Y.) plus 2 units human α-thrombin were added. In some wounds, $0.6-1.0 \times 10^6$ cultured porcine or human fibroblasts were carefully added to the bottom of the wound, prior to the addition of the fibrinogen-thrombin mixture. Since wounds were harvested at 3 or 4 days after fibroblast addition, rejection of xenoimplanted cells was never observed. In other wounds, human platelet releasate as a source of growth factors was added to the fibrinogen-thrombin mixture prior to its addition to the wound. Still other wounds received all additives. Wound sites were harvested 3 or 4 days after the additions.

Specimens from all wound sites were bisected vertically. One half was fixed in formalin, paraffin embedded, sectioned at 5 µm and stained with Masson trichrome to delineate morphologic alterations. The other half was placed in O.C.T.™ media, frozen in liquid nitrogen, stored in a −70° C. freezer, cryostat sectioned at 4 µm, picked up on fresh poly-L-lysine coated slides and processed for immunofluorescence studies.

Granulation tissue accumulation was quantified morphometrically as previously described (Clark et al. 1996). The first full section from the formalin-fixed half of each bisected wound specimen was mounted on a polylysine-coated slide and stained with Masson trichrome dye. These sections approximated the plane that vertically transected the center of each wound. The sections were numerically coded and visually evaluated on a Nikon BHK-2 microscope by an observer who had not participated in the animal experiments. Low power video images of histologic sections were transmitted to a Macintosh Quadra 800 via a RasterOps video card and Adobe Photoshop. The area of each section occupied by either granulation tissue or total-wound space was quantified by NIH Image software after tracing the respective areas of the digitized microscopic images. Percent granulation tissue for each wound was calculated by dividing the granulation tissue cross-sectional area by the total wound space cross-sectional area×100.

Human Fibrinogen and Platelet Releasate

Sterile, endotoxin-free human fibrinogen (New York Blood Center, New York, N.Y.) was >95% clottable and greater than 99% pure as assessed by silver-stained polyacrylamide gel electrophoresis.

Platelets were isolated from pooled human platelet packs according to previously described methods (Steed et al. 1992). Platelets pooled from 10–20 platelet packs were washed three times and suspended to a final concentration of $10^9$ platelets/ml in endotoxin free platelet buffer which contained 50 mM N-2-hydroxy-ethylpiperazine-N-2-ethanesulfonic acid (HEPES), 100 mM NaCl, 6 mM KCl and 3 mM glucose. Platelets were then incubated 10 minutes at room temperature with 1 unit bovine thrombin (Thrombinar, Armour Pharmaceutical, Kankakee, Ill.) per $10^9$ platelets. After granule release, the aggregated platelets were removed by centrifugation at 2,000×g for 10 minutes. The supernatant containing released platelet factors was heat treated for 10 hours at 60° C. and then stored frozen. For standardization of preparation, β-thromboglobulin and platelet factor-4 concentrations were determined by EIA kits obtained from American Bioproducts (Parsippany, N.J.).

Cultured Skin Fibroblasts for Wound Implantation

Porcine and human fibroblasts were cultured from explants of normal paravertebral and inframammary skin, respectively. Upon biopsy, tissue samples were placed in Dulbecco's minimal essential medium (DMEM) containing penicillin and streptomycin (100 units/ml and 100 µg/ml, respectively) and placed at 4° C. for use within 16 hours. To obtain fibroblast populations from dermis and from the septae of the subcutaneous fat, each biopsy was dissected parallel to the epidermal surface to yield four layers only the layers containing solely reticular dermis or solely subcutaneous fat were used for isolation of fibroblasts. The layers containing the interface between the epidermis and dermis and the interface between the dermis and subcutaneous fat were not used for this study.

Explants were made with 1 mm$^2$ fragments of the reticular dermis or subcutaneous fat layer. Each fragment was placed into an individual well of a 6 well tissue culture dish (Falcon or Nunc) and allowed to adhere for 8–10 min prior to the addition of DMEM containing 10% fetal bovine serum (Hyclone, Logan, UT), penicillin and streptomycin. The plates were then incubated in 7.5% $CO_2$ and 92.5% air with 95% humidity at 37° C. and medium was changed every 2–3 days. Outgrowth from each piece was detected within 7 days. Fibroblasts were then harvested by 0.1% trypsin and 0.001% EDTA and passaged at 70% confluence. Cells were either frozen in growth media and 10% DMSO or used for experimentation at passages 6–8.

Immediately prior to placement in wounds, cells were harvested and concentrated in sterile, endotoxin-free DMEM so that 20 µl contained 0.6–1.0×10$^6$ cells. After 20 µl aliquots of cells or medium without cells were added to the appropriate freshly created wounds, all sites were sealed with 150 µl of fibrin (see below). In some wounds platelet releasate was diluted 1:20 or 1:100 in a solution of 3 mg/ml fibrinogen (New York Blood Center, New York, N.Y.) in sterile, endotoxin-free saline. The undiluted platelet releasate used in these studies contained 135 µg/ml β-thromboglobulin and 90 µg/ml platelet factor-4.

Immunofluorescence Studies

Frozen sections were prepared for immunofluorescence as previously described (Folkvord et al. 1989). Antibodies were optimized for dilutions that gave maximal specific fluorescence and minimal background fluorescence on frozen tissue specimens. Since laminin can be detected at the tips of newly forming vessels during cornea neovascularization, and even on individual cells in advance of the tip (Jerdan et al. 1991), laminin was used to localize vessels in the porcine cutaneous wound models. In some double labeled immunofluorescence studies, rhodamine-conjugated anti-laminin antibodies (Gibco BRL, Grand Island, N.Y.) were combined either with mouse monoclonal IgM anti-vimentin (Sigma, St. Louis, Mo.), or with a mouse monoclonal IgG anti-αvβ3 antibody, 7G2 (Clark et al. 1996). The unlabeled primary antibodies were complexed with biotinylated-antibodies (Vector Laboratories, Burlingame, Calif.) to mouse IgM or IgG, respectively, and fluorescein-conjugated streptavidin (Folkvord et al. 1989). In other double label immunofluorescence studies, mouse monoclonal IgG anti-porcine CD-18 antibodies (VMRD, Inc, Pullman, Wash.) and TRITC-labeled goat anti-mouse IgG were combined with mouse monoclonal IgM anti-vimentin, biotinylated goat anti-mouse IgM and fluorescein-conjugated streptavidin. Vectashield mounting medium (Vector Laboratories, Burlingame, Calif.) was used to retard quenching. Slides were photographed on 35 mm TMAX™ 400 film (Eastman Kodak, Rochester, N.Y.) using a Nikon Microphot FXA epifluorescence microscope equipped with a halogen light source, a 470–490 nm excitation filter and a 515 nm barrier filter for fluorescein emission, and a 536–556 nm excitation filter and a 590 nm barrier filter for TRITC or rhodamine emission. The filters selected excluded cross excitation resulting in pure yellow/green fluorescein and red rhodamine/TRITC fluorescence.

It has previously been reported that no granulation tissue is observed in wounds during the first 3 days after excisional cutaneous injury (Welch et al. 1990). Subsequently, however, granulation tissue rapidly accumulates in wounds. Excisional wounds in normal porcine skin are 3±1.5% filled with granulation tissue by 4 days after injury, 48±14% filled by 5 days, and 88±20% filled at 7 days. This data derives from 5 replicate wounds on one Yorkshire pig and is representative of porcine excisional cutaneous wound repair in both Yorkshire and Minipig strains (Clark et al. 1996; McPherson et al. 1988).

Histologic sections of acute, normally healing wounds harvested at 0, 1, 3, and 5 days showed that in a fresh, day 0 wound there was a paucity of cells in the underlying subcutaneous tissue. The wound space was empty because the wound had been harvested immediately after wounding. One day later, clot was evident in the wound space and inflammatory cells had accumulated around the subdermal blood vessels, but no mesenchymal cell expansion had occurred. Although mesenchymal cells in the underlying subcutaneous tissue were markedly increased on day 3, clot filled the entire wound space as no granulation tissue had formed within the wound. By day 5, however, granulation tissue had filled the lower portion of the wound. Adipocytes were drawn into the wound space during healing, conceivably through the traction of the invading fibroblasts. Herniation of the subdermal tissue into the wound space seemed unlikely since this phenomenon was never observed in wounds prior to granulation tissue formation. The 3 day lag period prior to granulation tissue formation has been consistently observed in hundreds of wounds harvested over the past 10 years from dozens of Yorkshire and minipigs, regardless of age or sex.

Initially an investigation was conducted to determine whether fibrin matrix maturation might be the rate limiting step in granulation tissue ingress since tissue cells clearly accumulate at the base of 3 day wounds but fail to invade the clot. To examine this possibility, a reinjury wound model was developed in which wounds were allowed to heal for 5 or 7 days and then aggressively curetted to remove all granulation tissue. Surprisingly, wounds curetted on day 5 were 23±2% filled with granulation tissue 1 day later, 45±3% filled 2 days later, and 99±3% filled by 3 days after reinjury. The day 5 primed wound numbers represent data from 3 replicate wounds on 3 different animals for a total of 9 replicate wounds. Wounds curetted on day 7 were 47±4% filled 1 day later and essentially filled by 2 days after reinjury. The data for day 7 primed wounds derive from 3 replicates on one animal. This same animal also received 3 replicate day 5 primed wounds which were used in the day 5 primed wound tabulation. Since fresh fibrin clots were observed to form within curetted wounds, a 3 day delay prior to granulation tissue ingress should have occurred if fibrin matrix maturation was necessary.

Thus, it appeared that 5 and 7 day wounds are primed to produce granulation tissue at an extraordinary rate when reinjured. The rapid reaccumulation of granulation tissue was not an artifact of incomplete curetting since 5 and 7 day wounds harvested immediately after this procedure showed no residual granulation tissue. Histologically typical appearing granulation tissue rapidly accumulated in 1–3 days after curetting 5 and 7 day wounds.

Mesenchymal cell activation as a limiting step in granulation tissue formation would be consistent with the above findings. To address this directly, cultured porcine or human fibroblasts were grown to 80% confluence in DMEM plus 10% fetal bovine serum and added to freshly made wounds.

Fibroblasts grown under these conditions actively proliferate, express integrin cell surface receptors that recognize provisional matrix proteins such as fibronectin and vitronectin (Gailit et al. 1993), and secrete proteases, such as urokinase (Cullen et al. 1993) and matrix metalloproteinases (Circolo et al. 1991). Thus, cultured fibroblasts, which have presumably been activated by the in vitro conditions, phenotypically resemble wound fibroblasts more than resident dermal fibroblasts (Clark 1993a; Grinnell 1994).

The third day after injury was chosen as the ideal time to observe wounds for precocious granulation tissue accumulation since normally granulation tissue never developed prior to day 4 (Welch et al. 1990; Clark et al. 1996; McPherson et al. 1988). In fact, granulation tissue did not form in day 3 wounds, which had received either fibrin alone, fibrin and fibroblasts, or fibrin and platelet releasate. In contrast, a cellular infiltrate invaded the clot in wounds receiving fibrin, human fibroblasts, and platelet releasate. More particularly, after freshly made 8 mm full-thickness skin wounds were blotted to remove any blood, 150 $\mu$l of 3 mg/ml human fibrinogen and 2 units of thrombin in sterile, endotoxin-free normal saline was added (fibrin alone), plus $1 \times 10^6$ cultured porcine fibroblasts (fibrin and fibroblasts), 1:100 dilution of platelet releasate (fibrin and platelet releasate), or $1 \times 10^6$ cultured porcine fibroblasts and 1:100 dilution of platelet releasate (fibrin, fibroblasts, and platelet releasate). Images of the right basolateral edge of each wound taken with a 10x objective provided a closer view of the wound interface with underlying tissue. Although much cellular proliferation was noted in the subcutaneous tissue below 3 day wounds that had received fibrin, fibrin and fibroblasts, or fibrin and platelet releasate, no granulation tissue had formed within the wound. Nevertheless, fibroblasts were often noted to layer over the base of wounds receiving fibrin and fibroblasts. In contrast, wounds receiving fibrin, fibroblasts and platelet releasate developed a cellular infiltrate that invaded the wound space.

Normal granulation tissue is composed of both fibroblasts and new capillaries (Clark 1993a). The cellular infiltrate that invaded wounds receiving fibrin, fibroblasts and platelet releasates in 3 day wounds had these characteristics of granulation tissue on high-power examination using a 40x objective. Small blood vessels coursed vertically through a sea of fibroblast-like cells. The new granulation tissue appeared to arise either from the subcutaneous fat at the wound base as previously described for normal wound repair (Welch et al. 1990; Clark 1993a; Clark 1993b), or to emerge from the dermal-subcutaneous junction at the basolateral margin of the wound.

To confirm that the cell infiltrate in 3 day wounds receiving fibrin, fibroblasts and platelet releasate contained both fibroblasts and blood vessels, double-labeled immunofluorescence studies were done with fluorescein-ABC anti-vimentin that stains normal skin fibroblasts and endothelial cells, and rhodamine-conjugated anti-laminin that stains newly forming capillaries (Jerdan et al. 1991), as well as established blood vessels. Many fibroblasts intermixed with small blood vessels were present in the cell infiltrate invading 3 day wounds, to which fibrin, human fibroblasts and platelet releasate had been added. The granulation tissue appeared to emanate from the junction of the dermis and the subcutaneous tissue at the basolateral margin of the wound. Frozen tissue specimens from 3 day control wounds, which do not contain granulation tissue by Masson trichrome histology, did not contain fibroblasts or blood vessels in the wound space by double-label immunofluorescence probing.

To determine whether the newly forming tissue in 3 day wounds receiving fibrin, fibroblasts and platelet releasate contained mononuclear leukocytes as well as fibroblasts, Masson trichrome-stained tissue from wounds were analyzed with light microscopy using a 40x objective. While both mononuclear and polymorphonuclear leukocytes infiltrated the upper and mid-portions of the clot, the dense infiltration of cells penetrating the basal and basolateral perimeter of the clot en masse at day 3 were composed almost entirely of mononuclear cells that were either filiform fibroblast-like cells or round mononuclear cells. This pattern of cell infiltrate was similar to that observed in 4 and 5 day normally healing wounds. To confirm that mononuclear cell leukocytes as well as fibroblasts were infiltrating the clot perimeter in 3 day wounds receiving fibrin, fibroblasts and platelet releasate, wounds were examined by double-labeled immunofluorescence studies using fluorescein-ABC anti-vimentin and TRITC complexed anti-porcine CD18. Anti-vimentin stains normal skin fibroblasts, smooth muscle and endothelial cells brightly and leukocytes dimly, while anti-CD18 stains leukocytes brightly but not fibroblasts, smooth muscle and endothelial cells at all. When normally healing porcine wounds were stained with these antibodies, both vimentin (++), CD-18 (−) fibroblasts and vimentin (+), CD-18 (+) mononuclear leukocytes were observed to invade the clot perimeter en masse at day 5. Similarly the en masse cellular infiltrate at the clot perimeter of 3 day wounds receiving fibrin, fibroblasts and platelet releasate contained both vimentin (++), CD-18 (−) fibroblasts and vimentin (+), CD-18 (+) mononuclear leukocytes.

Recently it has been demonstrated that the capillary sprouts invading the fibrin-rich provisional matrix of porcine cutaneous wounds stain specifically and uniquely for $\alpha v \beta 3$, a provisional matrix integrin receptor (Clark et al. 1996). Therefore, granulation tissue induction in 3 day wounds receiving cultured fibroblasts, fibrin, and platelet releasate was further substantiated by the appearance of $\alpha v \beta 3$ on capillaries invading the fibrin clot. Granulation tissue and adjacent dermis were double-labeled for $\alpha v \beta 3$ and laminin. The capillaries that had invaded the clot expressed substantial $\alpha v \beta 3$ while the vessels in the adjacent dermis expressed relatively little $\alpha v \beta 3$. Both capillaries invading the clot and adjacent blood vessels in the dermis expressed laminin although laminin expression was less prominent in newly formed capillary sprouts as previously described (Clark et al. 1996).

Since the combination of cultured fibroblasts and platelet releasate in an exogenous fibrin clot induced nascent granulation tissue at day 3, this combination of substances was investigated for its ability to enhance granulation tissue accumulation 4 days after skin injury. Platelet releasate was added at a 1:20 or 1:100 dilution in the presence or absence of cultured human skin fibroblasts immediately after wounding. Four days later, wounds containing cultured fibroblasts plus 1:100 or 1:20 platelet releasate gave 7% or 14% granulation tissue fill of the wound space, respectively. When either cultured fibroblasts or platelet releasate was added alone, less than 4% granulation tissue accumulation was observed at 4 days. Control wounds containing only tissue culture medium or platelet releasate buffer accumulated less than 2% granulation tissue by 4 days after injury.

Excisional cutaneous wounds in tight-skinned animals, such as pigs and humans, heal the dermis by granulation tissue accumulation followed by granulation tissue contraction and then remodeling the cell-rich granulation tissue into a fibrous scar (Clark 1993a; Clark 1993b; Clark 1996). Mesenchymal cells do not begin to migrate into the fibrin clot-filled wound space until 4 days after injury. Surprisingly the reason for this 3 day lag phase has not been previously investigated. To investigate this, wounds which had healed for 5 or 7 days were reinjured by aggressive curetting to remove all accumulated granulation tissue from the wound space. If provisional matrix maturation was the rate limiting step in granulation tissue induction, the newly formed fibrin clot would be expected to require 3 days to mature. However, granulation tissue began to reaccumulate in the wound space within 24 hours after reinjury. In fact, wounds curetted on day 5 were completely filled with granulation tissue 3 days later. Wounds curetted on day 7 reaccumulated granulation tissue even faster, being half-filled by 24 hours and completely filled at 48 hours. Thus, fibrin clot maturation seemed unlikely as the rate limiting step in granulation tissue formation. In fact, reinjured wounds seemed to be primed for granulation tissue production, suggesting that mesenchymal cells in the surrounding skin might have been activated during the initial healing process.

To address this possibility directly, fibroblasts that were grown in tissue culture plastic dishes with serum-supplemented medium were tested for their ability to induce granulation tissue earlier than normally observed. In such culture conditions, fibroblasts proliferate and produce a pericellular fibronettin matrix: a phenotype that is readily reversible by the addition of collagen matrix (Xu and Clark 1996; Grinnell 1994; Sappino et al. 1990; Clark et al. 1995; Hynes 1973; Ruoslahti and Vaheri 1974; Yamada and Weston 1974). Thus, the fibroblasts used for this study come from an in vitro environment that simulates an early wound in which closely packed, proliferating fibroblasts are surrounded by fibronectin-rich provisional matrix and serum (Welch et al. 1990). Fibroblasts were grown to 80% confluence in 10% serum-supplemented medium, added to freshly made porcine full-thickness skin wounds, and then overlaid with an exogenous fibrin sealant. No granulation tissue was observed at 3 days. However, when the fibroblasts were sealed in the wound with fibrin to which platelet releasate was added, a cellular infiltrate that had characteristics of granulation tissue invaded the wound space 3 days after injury. The precocious appearance of granulation tissue was not induced by platelet releasate in fibrin without the addition of cultured fibroblasts.

Tissue cells accumulating in 3 day wounds, that had received cultured fibroblasts and platelet releasate, formed tissue similar, if not identical, to authentic granulation tissue as characterized by newly formed blood vessels coursing vertically among a bed of fibroblasts, the sine qua non of granulation tissue (Welch et al. 1990; Clark 1993a; Clark 1996). Both histologic sections and immunofluorescence studies confirmed the presence of these vertically oriented small blood vessels. Three day wounds were double-labeled with antibodies to vimentin, the major intermediate filament found in fibroblasts, and laminin, a major extracellular protein of blood vessels, to identify these components of granulation tissue. Recently it has been demonstrated that laminin is present at the tips of capillary sprouts during angiogenesis of the cornea, validating the utility of laminin as a marker even for newly forming capillaries (Jerdan et al. 1991). Indeed, small blood vessels, intercalated with numerous filiform-shaped vimentin positive cells, were observed in sites along the basolateral and basal wound margin where structures suggestive of newly formed granulation tissue were observed on histologic sections. In normal skin, such a plethora of fibroblasts is only typically observed in the papillary dermis, not in the reticular dermis or subcutaneous tissue.

In addition to fibroblasts and blood vessels, mononuclear leukocytes were present in the cell infiltrate invading the clot perimeter of day 3 wounds receiving fibrin, fibroblasts and platelet releasate. Thus, the combination of cell types present in the granulation-like tissue invading the clot of day 3 wounds receiving fibrin, fibroblasts and platelet releasate was similar to the admixture of fibroblasts, mononuclear leukocytes and blood vessels observed in normally healing day 5 porcine wounds (Welch et al. 1990; Clark et al. 1996) and consistent with previous observations that fibroblasts, mononuclear leukocytes and blood vessels invade the wound clot as a unit to form granulation tissue (Hunt 1980). The mononuclear leukocytes most likely represent activated macrophages which appear to play a critical role in sustaining granulation tissue formation by their ability to synthesize and secrete growth factors (Leibovich and Ross 1975; Knighton et al. 1983; Shimokado et al. 1985; Rappolee et al. 1988).

Recently, it has been demonstrated that $\alpha v \beta 3$, the extracellular matrix receptor for provisional matrix proteins such as fibrin, fibronectin, vitronectin, von Willebrand factor and thrombospondin (Hynes 1992; Yamada and Clark 1996), is required for angiogenesis (Brooks et al. 1994) and is expressed on capillary sprouts during invasive angiogenesis of granulation tissue formation (Clark et al. 1996). Here $\alpha v \beta 3$ was used as a marker for newly forming blood vessels. Indeed the blood vessels in the granulation tissue of 3 day wounds receiving cultured fibroblasts and fibrin sealant with platelet releasate contained small blood vessels invading the fibrin clot that were $\alpha v \beta 3$ positive.

Over the past decade, hundreds of cutaneous porcine wounds have been studied to which have been added numerous growth factors and extracellular matrix components both singly and in combination. In none of these experiments has granulation tissue formation been observed prior to day 4. Fibrin, cultured fibroblasts and platelet releasate is the first combination that has been found to elicit new tissue formation in day 3 cutaneous wounds. The new tissue has the cellular characteristics of granulation tissue since it contains fibroblasts, mononuclear leukocytes and activated blood vessels as observed in day 4 and 5 normally healing wounds. This is the first report of precocious granulation tissue induction in the literature, although many studies have shown increased granulation tissue at days 7 to 14 after addition of growth factors (Sporn et al. 1983; Lawrence et al. 1986; Lynch et al. 1989; Pierce et al. 1989; Greenhalgh et al. 1990; Mustoe et al. 1991; Pierce et al. 1992).

EXAMPLE II

In Vitro Model

Materials

Recombinant PDGF-BB (platelet-derived growth factor) was obtained from ZymoGenetics (Seattle, Wash.) and platelet releasate was obtained from Curative Technologies (East Setauket, N.Y.). ϵ-Amino-n-Caproic acid (ϵ-ACA) was purchased from Sigma (St. Louis, Mo.). Trasylol® (Aprotinin, 100,000 KIU/ml) and bovine serum albumin (BSA, fatty acid free, fraction V) were purchased from Miles (Kankakee, Ill.). Tissue culture plastic flasks were from Costar (Cambridge, Mass.). GRGDSP (SEQ ID NO:1) and GRGESP (SEQ ID NO:2) were synthesized using the ABI Model 431A peptide synthesizer and FastMoc chemistry at the Center for Analysis and Synthesis of Macromolecules (SUNY, Stony Brook).

Determination of PDGF Content

PDGF concentrations in platelet releasate were determined using a sandwich enzyme immunoassay EIA. High-binding microtiter plates (Corning Corp., Corning, N.Y.) were coated overnight at 4° C. with 2 µg/ml goat anti-PDGF IgG (Collaborative Research Inc., Bedford, Mass.) in phosphate-buffered saline (PBS). Three washes in PBS with 0.1% Tween-20 were performed after this incubation and between each of the following incubations. The plate was blocked with 1% BSA, 0.1% Tween-20 in PBS (PBS+AT) for 1 hour at 37° C. Samples, and PDGF-AB (Boehringer Mannheim, Indianapolis, Ind.) for the standard curve, were diluted in PBS+AT and incubated in the plate for 2 hours at 37° C. The secondary antibody was 2.5 µg/ml of a 1:1 mixture of rabbit anti-PDGF-AA and anti-PDGF-BB (Genzyme, Boston, Mass.). After incubating for 1 hour at 37° C. with the secondary antibody, the plate was again incubated for 1 hour at 37° C. with 0.5 µg/ml goat anti-rabbit IgG horseradish peroxidase conjugate (Kirkegaard & Perry, Gaithersberg, Md.). The plate was incubated for 10 minutes at room temperature with 3,3',4,4' tetramethylbenzidine peroxidase substrate, and absorbance measured at 450 nm. The undiluted platelet releasate preparation used here contained 15 ng/ml PDGF-BB.

Antibodies

Anti-$\beta$1 (MoAb #13), anti-$\alpha$5$\beta$1 (MoAb #16), and ES46-8, an anti-chicken integrin antibody used as control, were obtained from the National Institute of Dental Research (Bethesda, Md.) (Akiyama et al. 1989). Rabbit anti-fibronectin was obtained from DAKO (Carpinteria, Calif.). Alkaline phosphatase conjugated goat anti-rabbit antibody was from Cappel/Organon Teknika (Durham, N.C.).

Fibrinogen

Human fibrinogen (FN) was obtained from Calbiochem (San Diego, Calif.). To prevent fibrinolysis, plasminogen was removed from the fibrinogen by passage through a lysine-Sepharose 4B column (Pharmacia, Piscataway, N.J.) (Deutsch and Mertz 1970). To remove contaminating FN, plasminogen-depleted fibrinogen was further passed through a gelatin-Sepharose 4B column (Pharmacia, Piscataway, N.J.) (Engvall and Ruoslahti 1977). The removal of FN was confirmed by SDS-PAGE and ELISA. The clottability before and after treatment with lysine-Sepharose 4B and gelatin-Sepharose 4B was over 90%.

Cells

Primary cultures of human adult dermal fibroblasts were cultured in Dulbecco's modified Eagle's medium (DMEM, Life Technologies) supplemented with 100 U/ml penicillin and 100 µg/ml streptomycin, 42 mmol/l sodium bicarbonate and 10% fetal bovine serum (FBS, Atlanta Biologicals, Norcross, Ga.) at 37° C. and 5% $CO_2$/95% air in a humidified atmosphere. The cells were used between passages 4 and 12.

Irradiation

To inhibit cell proliferation, fibroblasts were suspended in DMEM+10% FBS and $\gamma$-irradiated for 3.2 min using a $^{137}$Cs source (3000 rad, Acel Gammacell 1000 B). For cell number and viability determinations, irradiated and non-irradiated cells were seeded in a 24-well plate at a density of $1\times10^4$ cells/well in DMEM+10% FBS and then cultured for up to 7 days. The cell number and viability were determined every 24 hours by trypan blue exclusion.

Preparation of Floating, Contracted Collagen Gels

Fibroblast cultures at 80% confluence were harvested by treatment with 0.05% trypsin/0.02% EDTA (ethylenediaminetetraacetic acid). Trypsin was inactivated by addition of soy bean trypsin inhibitor in PBS containing 0.2% BSA. The cells were washed twice with DMEM+10% FBS and resuspended at a concentration of $1\times10^6$ cells/ml. The fibroblasts were mixed with DMEM (5x), 10% FBS and neutralized collagen (Vitrogen 100, Celtrix Labs., Santa Clara, Calif.). In some experiments, FBS was replaced by 30 ng/ml PDGF-BB and 2% BSA. 0.6 ml aliquots of the cell mixture were added to the wells of a 24-well tissue culture plate, precoated with 2% BSA, and the collagen was allowed to polymerize at 37° C. The final concentration of collagen was 1.8 mg/ml and each gel contained $6\times10^4$ cells. After two hours incubation, the gels were gently detached from the plastic surface to allow contraction, 0.5 ml DMEM+10% FBS was added, and the gels were incubated overnight at 37° C. in 5% $CO_2$.

Preparation of Dried Fibrin Fibrils

Fibrinogen was mixed with DMEM (5x) and 0.5 U/ml thrombin (New York Blood Center, New York, N.Y.) so that the final concentration of fibrinogen was 300 µg/ml. Aliquots of 450 µl were added to the wells of a 24-well plate, and after a 2 hour incubation at 37° C. in 5% $CO_2$, the polymerized gels were dried overnight at room temperature under sterile conditions.

Preparation of Two- and Three-dimensional Migration Models

Two-dimensional Outmigration Model

Dried fibrin fibril-coated dishes were washed once with PBS and contracted collagen gels were placed on the surface. The collagen gels were surrounded with DMEM so that the medium was level with the top of the collagen gel.

Three-dimensional Transmigration Model

Figure 1:
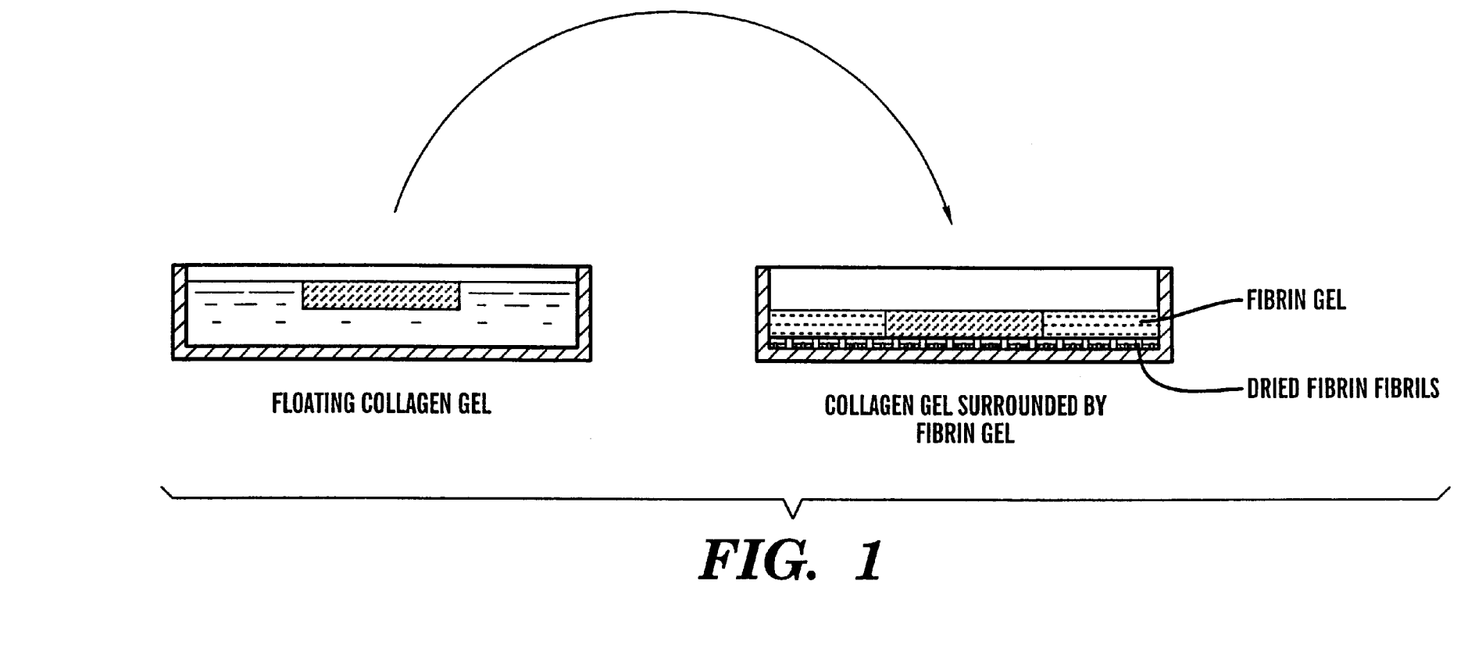
FIG. 1 illustrates the formation of the three dimensional in vitro model of the subject invention for assaying cell transmigration from a collagen gel into a fibrin gel.

Dried fibrin fibril-coated dishes were washed once with PBS and contracted collagen gels were placed on the surface. Fibrinogen, at a final concentration of 300 µg/ml, was mixed with DMEM (5x) and 1.0 U/ml thrombin. When needed, other supplements, such as growth factors, were added to the mixture. The collagen gels were surrounded with the fibrinogen solution so that the fibrin gel was level with the collagen gel (FIG. 1)

Evaluation

The number of migrated cells was evaluated under a Nikon inverted phase microscope by counting identifiable cell nuclei located outside of the contracted collagen gel, either on the fibrin fibril substrate (two-dimensional model) or within the fibrin gel (three-dimensional model). Each condition was assayed in triplicate and experiments were repeated at least three times.

Porcine Cutaneous Wound Model

Full-thickness excisional wounds were made by an 8-mm circular punch into the paravertebral skin of Minipigs. The wounds were dressed with Tegaderm, a polyurethane occlusive dressing, and harvested 1 and 3 days later as previously described (Welch et al. 1990).

Histology and Immunohistochemistry

Specimens from all wound sites were bisected-vertically. One half was fixed in formalin, paraffin embedded, sectioned at 5 µm, and stained with Masson trichrome to delineate morphological alterations. For immunohistochemistry the deparaffinized sections were first incubated with 0.4% pepsin in 0.1 mol/l HCl (Folkvord et al. 1989). Intrinsic peroxidase was blocked with 3% $H_2O^2$ and non-specific antibody binding with 2% skim milk. Sections were incubated with the primary antibody (anti-fibronectin) for 1.5 hours at room temperature, followed by a 1.5 hour incubation with alkaline phosphatase conjugated anti-rabbit immunoglobulin. Finally, sections were covered with Fast Red® (BioGenex, San Ramon, Calif.) until red stain developed and then counterstained with hematoxylin.

The specific purpose of this example was to establish a defined in vitro model for the early cutaneous wound. The basis of this model is a contracted collagen gel containing fibroblasts which acquire a tissue-like phenotype within the collagen matrix. Surrounding the collagen gel, or dermal equivalent, with a fibrin clot produces a simple inside-outside model of the early cutaneous wound (FIG. 1). Without an added stimulus, no more than a few of the normal adult human dermal fibroblasts within the collagen gel migrated into the fibrin gel. However, transmigration of fibroblasts from the collagen gel into the fibrin gel could be induced by platelet releasate (PR) or recombinant PDGF-BB in a concentration-dependent manner. Cells were found at levels throughout the fibrin gel, not only at the bottom. Cells migrating in response to the highest doses of platelet releasate or PDGF-BB were often interconnected by extended cell processes. For the subsequent experiments described below, fibroblasts were stimulated either with platelet releasate at a dilution of 1:10 or with PDGF-BB at a concentration of 30 ng/ml. The physiological concentration of fibrinogen in plasma is 3 mg/ml. The number of transmigrated cells was approximately the same if fibrinogen was used at the physiological concentration or at 300 µg/ml. Therefore, in the following experiments 300 µg/ml fibrinogen was used.

Since it is well known that both platelet releasate and PDGF are mitogenic for fibroblasts (Ross and Raines 1990), the number of migrated cells was always counted after only one day, minimizing the effect of cellular proliferation. To verify that at this time point proliferation did not make a significant contribution to the accumulation of cells within the fibrin, irradiated cells were used in the preparation of the collagen gels. After irradiation these cells remained more than 95% viable but did not proliferate over the course of 7 days. Furthermore, irradiation did not impair the cells' ability to contract the collagen gels. Most importantly, irradiation had very little effect on the number of cells that migrated in response to platelet releasate or PDGF-BB.

Plasminogen and its activators have been shown to be necessary for fibroblast invasion of fibrin in a different migration assay (Knox et al. 1987). Two protease inhibitors were used to investigate if proteases are required for fibroblast transmigration in the model described here. Trasylol®, or aprotinin, inhibits many serine proteases (Fritz and Wunderer 1983) and it is particularly effective against plasmin (Longstaff 1994). ε-Aminocaproic acid (ε-ACA) is a lysine analog which interacts with the active site of plasmin and seems to prevent association of plasmin(ogen) and tissue plasminogen activator (Iwamoto 1975). Transmigration induced by PDGF-BB was inhibited by ε-ACA and Trasylol® in a concentration-dependent manner. Invasion of the fibrin gel was reduced about 80% by 500 µg/ml ε-ACA or by 400 KIU/ml Trasylol®. To determine of proteases are only necessary for invasion of the fibrin gel, or if they are also required for exit from the collagen gel, the same protease inhibitors were tested in a closely related model system in which the collagen gel was attached to a fibrin substrate, as usual, but then surrounded with liquid culture medium instead of a fibrin gel. In this system, outmigration onto dried fibrin fibrils induced by PDGF-BB was not inhibited by ε-ACA or by Trasylol®.

The next series of experiments examined the role of FN in the transmigration process. Knox et al. (Knox et al. 1986) previously showed that fibroblast invasion of a fibrin clot in vitro was dependent on FN. However, in more recent studies (Brown et al. 1993) fibroblast invasion of fibrin was found to be independent of FN. In vivo wound studies, however, have revealed that FN always accompanies fibrin in the clot provisional matrix (Grinnell et al. 1980; Clark et al. 1981). The results herein show that in porcine cutaneous wounds fibrin and FN permeate the periwound stroma on the third day after injury. Since fibroblast migration into cutaneous wounds does not commence until the fourth day after injury, the FN accumulation in the collagenous matrix may facilitate fibroblast migration. To determine whether FN either in the fibrin gel or in the collagen gel is required for fibroblast transmigration in this model, FN was selectively removed from the fibrinogen and from the collagen. First, residual FN was removed from the fibrinogen preparation by affinity chromatography on gelatin. After removal of the FN, fibroblast transmigration into the fibrin clot was decreased by about 80w. The normal amount of transmigration could be restored by adding 30 µg/ml FN to the fibrin gel to produce a FN:fibrinogen ratio of 1:10, which is also the physiological ratio in plasma. Second, exogenous FN was completely excluded from the model system by omitting serum from the collagen gel preparation and substituting PDGF-BB, which is equally effective at stimulating fibroblast-driven collagen gel-contraction (Clark et al. 1989). In experiments with FN-free collagen gels and FN-free fibrin gels, no transmigration occurred. Transmigration was only re-established at the full amount by addition of FN to both the collagen gel and the fibrin gel, and the concentration of 30 µg/ml FN in each gel seemed the most effective.

In the early phase of wound repair, when migration is initiated, the concentration of $Mg^{2+}$ is elevated and that of $Ca^{2+}$ is reduced (Grzesiak and Pierschbacher 1995). As a result, the ratio of $Mg^{2+}:Ca^{2+}$ is over 1 in early wounds, while the ratio in normal plasma is 0.4. Therefore, an investigation was conducted to determine whether, under concentrations of $Mg^{2+}$ and $Ca^{2+}$ found in early wound fluid, transmigration could be stimulated even in the absence of FN. The results showed that increasing the $Mg^{2+}$-concentration from 0.8 to 1.4 mmol/l could not stimulate fibroblasts to transmigrate .into a FN-depleted fibrin gel. Migration was increased into a FN containing fibrin gel at the higher $Mg^{2+}/Ca^{2+}$ ratio but this did not reach statistical significance (p=0.23).

Since fibroblast transmigration was dependent on FN, and since many cell receptors for FN recognize the arginine-glycine-aspartate (RGD) sequence within the FN molecule, the inhibitory effect of RGD peptides upon transmigration was measured. The synthetic peptide GRGDSP (SEQ ID NO:1) was added to the fibrin gel, and fibroblast transmigration was stimulated by PR or PDGF-BB. Transmigration was inhibited, in a concentration-dependent manner, by GRGDSP (SEQ ID NO:1) but not by the control-peptide GRGESP (SEQ ID NO:2).

Several different integrins can bind to the RGD site within FN. On normal human dermal fibroblasts, however, the integrin α5β1 serves as the primary receptor for FN (Gailit et al. 1993; Gailit and Clark 1996). Monoclonal antibodies against the integrin β1 subunit and against integrin α5β1 strongly inhibited transmigration. At 10 µg/ml, anti-β1 and anti-α5β1 each inhibited transmigration by 90% and the combination of both antibodies completely eliminated it. A control antibody had no effect on the migration induced by PDGF-BB. Thus, it appears that the classic FN receptor α5β1 contributes to the transmigration of human dermal fibroblasts from a collagen gel dermal equivalent into a fibrin clot provisional matrix.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

REFERENCES

Akiyama, S. K., et al., J Cell Biol 109:863–875 (1989).
Bell, E., et al., Proc Natl Acad Sci USA 76:1274–1278 (1979).
Berthod, F., et al., Biomaterials 14:749–754 (1993).
Brooks, P. C., et al., Science 264:569–571 (1994).
Brown, L. F., et al., Amer J Pathol 142:273–283 (1993).
Circolo, A., et al., J Biol Chem 266:12283–12288 (1991).
Clark, R. A. F., Am J Med Sci 306:42–48 (1993a).
Clark, R. A. F., In: *Dermatology in General Medicine*, 4th ed. (Fitzpatrick, T. B., et al., eds), McGraw-Hill Book Company, New York, N.Y. (1993b), pp. 473–483.
Clark, R. A. F., In: *Molecular and Cell Biology of Wound Repair*, 2nd ed. (Clark, R. A. F., ed), Plenum Press, New York, N.Y. (1996), pp. 3–50.
Clark, R. A. F., et al., J Invest Dermatol 79:264–269 (1981).
Clark, R. A. F., et al., J Invest Dermatol 70:264–269 (1982a).
Clark, R. A. F., et al., J Invest Dermatol 79:269–276 (1982b).
Clark, R. A. F., et al., J Exp Med 156:646–651 (1982c).
Clark, R. A. F., et al., J Clin Invest 84:1036–1040 (1989).
Clark, R. A. F., et al., J Cell Sci 108:1251–1261 (1995).
Clark, R. A. F., et al., Am J Path 148:1407–1421 (1996).
Cullen, B., et al., Clin Res 41:608A (1993).
Deutsch, D. G., and Mertz; E. T., Science 170:1095–1096 (1970).
Eckes, B., et al., FEBS Lett 318:129–133 (1993).
Elices, M. J., et al., J Cell Biol 112:169–181 (1991).
Elsdale, T., and Bard, J., J Cell Biol 54:626–637 (1972).
Engvall, E., and Ruoslahti, E., Int J Cancer 20:1–5 (1977).
Folkvord, J. M., et al., J Histochem Cytochem 37:105–113 (1989).
Fritz, H., and Wunderer, G., Arzneim-Forsch/Drug Res 33:479–494 (1983).
Gailit, J., and Clark, R. A. F., J Invest Dermatol 106:102–108 (1996).
Gailit, J., et al., J Invest Dermatol 100:323–328 (1993).
Graham, M. F., et al., Proc Soc Exp Biol Med 176:302–308 (1984).
Greenhalgh, D. G., et al., Am J Path 136:1235–1246 (1990).
Grinnell, F., et al., Cell 19:517–525 (1980).
Grinnell, F., J Cell Biol 124:401–404 (1994).
Grzesiak, J. J., and Pierschbacher, M. D., J Clin Invest 95:227–233 (1995).
Hay, E. D., In: *Cell Biology of the Extracellular Matrix* (E. Hay, ed), Plenum Press, New York, N.Y. (1991), pp. 419–462.
Hsieh, P., and Chen, L., J Cell Biol 96:1208–1217 (1983).
Hunt, T. K., *Wound Healing and Wound Infection: Theory and Surgical Practice*, Appleton-Century-Crofts, New York, N.Y. (1980).
Hynes, R. O., Proc Natl Acad Sci USA 70:3170–3174 (1973).
Hynes, R. O., Cell 69:11–25 (1992).
Iwamoto, M., Thromb Diath Haemostas 33:573–585 (1975).
Jerdan, J. A., et al., Microvasc Res 42:255–265 (1991).
Klein, C. E., et al., J Cell Biol 115:1427–1436 (1991).
Knighton, D. R., et al., Science 221:1283–1285 (1983).
Knox, P., et al., J Cell Biol 102:2318–2323 (1986).
Knox, P., et al., J Cell Physiol 132:501–508 (1987).
Lawrence, W. T., et al., Ann Surgery 203:142–147 (1986).
Leibovich, S. J., and Ross, R., Am J Pathol 78:71–100 (1975).
Lin, Y.-C., and Grinnell, F., J Cell Biol 122:663–672 (1993).
Longstaff, C., Blood Coag Fibrinol 5:537–542 (1994).
Lorand, L., Ann NY Acad Sci 202:6–30 (1972).
Lynch, S.E., et al., J Clin Invest 84:640–646 (1989).
Mauch, C., et al., Exp Cell Res 178:493–530 (1988).
McPherson, J. M., et al., Coll Rel Res 8:83–100 (1988).
Montesano, R., et al., J Cell Physiol 132:509–516 (1987).
Mosesson, M. W., et al., Proc Natl Acad Sci USA 86:1113 (1989).
Mosher, D. F., J Biol Chem 250:6614–6621 (1975).
Mosher, D. F., J Biol Chem 251:1639–1645.(1976).
Mosher, D. F., and Johnson, R. B., Ann NY Acad Sci 408:583–594 (1983).
Mustoe, T. A., et al., J Clin Invest 87:694–703 (1991).
Nakagawa, S., et al., Exp Cell Res 182:2572–2582 (1989).
Nishiyama, T., et al., Matrix 10:412–419 (1990).
Nusgens, B., et al., Collagen Relat Res 4:351–363 (1984).
Pierce, G. F., et al., J Cell Biol 109:429–440 (1989).
Pierce, G. F., et al., Am J Path 140:1375–1388 (1992).
Pierschbacher, M. D., and Ruoslahti, E., J Biol Chem 262:17294–17298 (1987).
Pisano, J. J., et al., Science 160:892–893 (1968).
Putnam, A. J., and Mooney, D. J., Nature Medicine 2:824–826 (1996).
Rappolee, D. A., et al., Science 241:708–712 (1988).
Ross, R., and Raines, E. W., In: *Growth Factors: From Genes to Clinical Application*, (V. Sara, ed), Raven Press, New York N.Y. (1990), pp. 193–199.
Ross, R., et al., Phil Trans R Soc Lond B 327:155–169 (1990).
Ross, R., et al., Cell 46:155–169 (1986).
Ruoslahti, E., J Clin Invest 87:1–5 (1991).
Ruoslahti, E., and Vaheri, A., Nature 248:789–791 (1974).
Sappino, A. P., et al., Lab Invest 63:144–164 (1990).
Sarber, R., et al., Mech Ageing Dev 17:107–117 (1981).
Schor, S. L., et al., J Cell Sci 48:301–314 (1981).
Senior, R. M., et al., J Cell Biol 96:382–385 (1983).
Senior, R. M., et al., J Cell Biol 100:351–356 (1985).
Seppa, H. E. J., et al., J Cell Biol 92:584–588 (1982).
Shainoff, J. R., et al., J Biol Chem 166:6429–6437 (1991).
Shaw, R. J., et al., J Cell Biol 111:2139–2148 (1990).
Shimokado, K., et al., Cell 43:277–286 (1985).
Siebenlist, K. R., and Mosesson, M. W., Biochemistry 31:936 (1992).
Smith, J. W., et al., J Biol Chem 265:12267–12271 (1990).
Sporn, M. B., and Roberts, A. M., J Cell Biol 119:1017–1021 (1992).
Sporn, M. B., et al., Science 219:1329–1331 (1983).
Steed, D. L., et al., Diabetes Care 15:1598–1604 (1992).
Streuli, C. H., et al., J Cell Biol 129:591–603 (1995).
Tonnesen, M. G., et al., In: *Molecular and Cellular Biolocy of Wound Repair* (Clark, R. A. F. and Henson, P. M., eds), Plenum Press, New York (1988), pp. 149–183.
Tremble, P., et al., J Cell Biol 129:1707–1720 (1995).
Unemori, E. N., and Werb, Z., J Cell Biol 103:1021–1031 (1986).
Welch, M. P., et al., J Cell Biol 110:133–145 (1990).
Xu, J., and Clark, R. A. F., J Cell Biol 132:239–249 (1996).
Yamada, K. M., and Clark, R. A. F., In: *Molecular and Cellular Biology of Wound Repair*, 2d ed. (Clark, R. A. F., ed), Plenum Press, New York (1996), pp. 311–338.
Yamada, K. M., and Weston, J. A., Proc Natl Acad Sci USA 71:3492–3496 (1974).

What is claimed is:

1. An in vivo model for cell migration comprising:
   an animal model, wherein the animal model is a mammal, having a naturally occurring first extracellular matrix having a cell added thereto, said first extracellular matrix representing a first natural environment in which said cell naturally resides; and
   a second extracellular matrix in physical contact with said first extracellular matrix, said second extracellular matrix simulating a second natural environment into which said cell naturally migrates from said first natural environment, wherein said second extracellular matrix has been added to the animal model.

2. The in vivo model of claim 1, wherein said cell comprises a fibroblast.

3. The in vivo model of claim 2, wherein said fibroblast is a dermal skin fibroblast.

4. The in vivo model of claim 2, wherein said fibroblast comprises a subcutaneous skin fibroblast.

5. The in vivo model of claim 1, wherein said cell comprises an endothelial cell.

6. The in vivo model of claim 1, wherein said cell comprises a monocyte/macrophage.

7. The in vivo model of claim 1, wherein said first natural environment comprises a collagenous stroma.

8. The in vivo model of claim 1, wherein said second natural environment comprises fibrin.

9. The in vivo model of claim 8, wherein said second extracellular matrix comprises arfibrin gel.

10. The in vivo model of claim 8, wherein said second extracellular matrix comprises an artificial extracellular matrix.

11. The in vivo model of claim 8, wherein said second extracellular matrix includes fibronectin.

12. The in vivo model of claim 8, wherein said second extracellular matrix includes hyaluronic acid.

13. The in vivo model of claim 1, further comprising:
    a plurality of cells positioned between said first extracellular matrix and said second extracellular matrix.

14. A method of screening substances for the effect of such substances on cell migration, said method comprising:
    providing an in vitro model for cell migration, said in vitro model comprising:
      a first extracellular matrix having a cell added thereto, said first extracellular matrix simulating a first natural environment in which said cell naturally resides; and
      a second extracellular matrix in physical contact with said first extracellular matrix, said second extracellular matrix simulating a second natural environment into which said cell naturally migrates from said first natural environment;
    determining a rate of first migration of said cells from said first extracellular matrix of said in vitro model into said second extracellular matrix of said in vitro model;
    adding a substance to said in vitro model;
    determining a rate of second migration of said cells from said first extracellular matrix of said in vitro model into said second extracellular matrix of said in vitro model after addition of said substance, wherein an increase from the rate of first migration in said in vitro model to the rate of second migration in said in vitro model indicates that the substance increases cell migration in said in vitro model, and wherein a decrease from the rate of first migration in said in vitro model to the rate of second migration in said in vitro model indicates that the substance decreases cell migration in said in vitro model; and
    providing an in vivo model for cell migration, said in vivo model comprising:
      an animal model, wherein the animal is a mammal, comprising a naturally occurring first extracellular matrix having a cell added thereto; and a second extracellular matrix in physical contact with said first extracellular matrix, wherein said second extracellular matrix has been added to the animal model;

determining a rate of first migration of said cells from said first extracellular matrix of said in vivo model into said second extracellular matrix of said in vivo model;

adding a substance to said in vivo model; and determining a rate of second migration of said cells from said first extracellular matrix of said in vivo model into said second extracellular matrix of said in vivo model after addition of said substance to said in vivo model, wherein an increase from the rate of first migration in said in vivo model to the rate of second migration in said in vivo model indicates that the substance increases cell migration, and wherein a decrease from the rate of first migration in said in vivo model to the rate of second migration in said in vivo model indicates that the substance decreases cell migration.

15. The method of claim 14 further comprising:

providing a plurality of cells positioned between said first extracellular matrix and said second extracellular matrix of said in vivo model;

determining another rate of first migration of said plurality of cells from between said first extracellular matrix and said second extracellular matrix into said second extracellular matrix in said in vivo model; and determining another rate of second migration of said plurality of cells from between said first extracellular matrix and said second extracellular matrix into said second extracellular matrix after addition of said substance to said in vivo model, wherein an increase from the another rate of first migration to the another rate of second migration indicates that the substance increases cell migration, and wherein a decrease from the another rate of first migration to the another rate of second migration indicates that the substance decreases cell migration in said in vivo model.

16. A method of screening for substances that affect cell migration, said method comprising:

providing an in vivo model for cell migration, said in vivo model comprising:

an animal model, wherein the animal is a mammal, having a naturally occurring first extracellular matrix having a cell added thereto, said first extracellular matrix representing a first natural environment in which said cell naturally resides; and a second extracellular matrix in physical contact with said first extracellular matrix, said second extracellular matrix simulating a second natural environment into which said cell naturally migrates from said first natural environment, wherein said second extracellular matrix has been added to the animal model;

determining a rate of first migration of said cells from said first extracellular matrix into said second extracellular matrix in said in vivo model;

adding a substance to said in vivo model; and determining a rate of second migration of said cells from said first extracellular matrix into said second extracellular matrix after addition of said substance to said in vivo model, wherein an increase from the rate of first migration to the rate of second migration indicates that the substance increases cell migration, and wherein a decrease from the rate of first migration to the rate of second migration indicates that the substance decreases cell migration in said in vivo model.

17. The method of claim 16 further comprising:

providing a plurality of cells positioned between said first extracellular matrix and said second extracellular matrix of said in vivo model;

determining another rate of first migration of said plurality of cells from between said first extracellular matrix and said second extracellular matrix into said second extracellular matrix in said in vivo model; and determining another rate of second migration of said plurality of cells from between said first extracellular matrix and said second extracellular matrix into said second extracellular matrix after addition of said substance to said in vivo model, wherein an increase from the another rate of first migration to the another rate of second migration indicates that the substance increases cell migration, and wherein a decrease from the another rate of first migration to the another rate of second migration indicates that the substance decreases cell migration in said in vivo model.

18. A method of screening for substances that affect cell migration, said method comprising:

providing a cell and a first and second extracellular matrix;

determining that said cell can move on said first extracellular matrix and said second extracellular matrix;

providing an in vitro model for cell migration, said in vitro model comprising:

said first extracellular matrix having a cell added thereto, said first extracellular matrix simulating a first natural environment in which said cell naturally resides; and said second extracellular matrix in physical contact with said first extracellular matrix, said second extracellular matrix simulating a second natural environment into which said cell naturally migrates from said first natural environment;

determining a rate of first migration of said cells from said first extracellular matrix of said in vitro model into said second extracellular matrix of said in vitro model;

adding a substance to said in vitro model; and determining a rate of second migration of said cells from said first extracellular matrix of said in vitro model into said second extracellular matrix of said in vitro model after addition of said substance, wherein an increase from the rate of first migration to the rate of second migration in said in vitro model indicates that the substance increases cell migration in said in vitro model, and wherein a decrease from the rate of first migration to the rate of second migration in said in vitro model indicates that the substance decreases cell migration in said in vitro model; and providing an in vivo model for cell migration, said in vivo model comprising:

an animal model, wherein the animal is a mammal, comprising a naturally occurring first extracellular matrix having a cell added thereto; and said second extracellular matrix in physical contact with said first extracellular matrix, wherein said second extracellular matrix has been added to the animal model;

determining a rate of first migration of said cells from said first extracellular matrix of said in vivo model into said second extracellular matrix of said in vivo model;

adding a substance to said in vivo model; and determining a rate of second migration of said cells from said first extracellular matrix of said in vivo model into said second extracellular matrix of said in vivo model after addition of said substance to said in vivo model, wherein an increase from the rate of first migration in said in vivo model to the rate of second migration in said in vivo model indicates that the substance increases cell migration, and wherein a decrease from the rate of first migration in said in vivo model to the rate of second migration in said in vivo model indicates that the substance decreases cell migration.

19. The method of claim 18 further comprising:

providing a plurality of cells positioned between said first extracellular matrix and said second extracellular matrix of said in vivo model;

determining another rate of first migration of said plurality of cells from between said first extracellular matrix and said second extracellular matrix into said second extracellular matrix in said in vivo model; and determining another rate of second migration of said plurality of cells from between said first extracellular matrix and said second extracellular matrix into said second extracellular matrix after addition of said substance to said in vivo model, wherein an increase from the another rate of first migration to the another rate of second migration indicates that the substance increases cell migration, and wherein a decrease from the another rate of first migration to the another rate of second migration indicates that the substance decreases cell migration in said in vivo model.

20. A method of screening for substances that affect cell migration, said method comprising:

providing a cell and a first and second extracellular matrix;

determining that said cell can move on said first extracellular matrix and said second extracellular matrix;

providing an in vivo model for cell migration, said in vivo model comprising:
an animal model, wherein the animal is a mammal, having a naturally occurring first extracellular matrix having a cell added thereto, said first extracellular matrix representing a first natural environment in which said cell naturally resides; and
a second extracellular matrix in physical contact with said first extracellular matrix, said second extracellular matrix simulating a second natural environment into which said cell naturally migrates from said first natural environment, wherein said second extracellular matrix has been added to the animal model;

determining a rate of first migration of said cells from said first extracellular matrix into said second extracellular matrix in said in vivo model;

adding a substance to said in vivo model; and determining a rate of second migration of said cells from said first extracellular matrix into said second extracellular matrix after addition of said substance to said in vivo model, wherein an increase from the rate of first migration to the rate of second migration indicates that the substance increases cell migration, and wherein a decrease from the rate of first migration to the rate of second migration indicates that the substance decreases cell migration in said in vivo model.

21. The method of claim 20 further comprising:

providing a plurality of cells positioned between said first extracellular matrix and said second extracellular matrix of said in vivo model;

determining another rate of first migration of said plurality of cells from between said first extracellular matrix and said second extracellular matrix into said second extracellular matrix in said in vivo model; and determining another rate of second migration of said plurality of cells from between said first extracellular matrix and said second extracellular matrix into said second extracellular matrix after addition of said substance to said in vivo model, wherein an increase from the another rate of first migration to the another rate of second migration indicates that the substance increases cell migration, and wherein a decrease from the another rate of first migration to the another rate of second migration indicates that the substance decreases cell migration in said in vivo model.

22. A method of screening extracellular matrices for the effect of such extracellular matrices on cell migration, said method comprising:

providing an in vivo model for cell migration, said in vivo model comprising:
an animal model, wherein the animal is a mammal, having a naturally occurring first extracellular matrix having a cell added thereto, said first extracellular matrix representing a first natural environment in which said cell naturally resides; and
a second extracellular matrix in physical contact with said first extracellular matrix, said second extracellular matrix comprising a fibrin gel;

determining a rate of first migration of said cells from said first extracellular matrix into said second extracellular matrix;

substituting an artificial extracellular matrix for said second extracellular matrix in said in vivo model; and determining a rate of second migration of said cells from said first extracellular matrix into said artificial extracellular matrix, wherein an increase from the rate of first migration to the rate of second migration indicates that said artificial extracellular matrix increases cell migration, and wherein a decrease from the rate of first migration to the rate of second migration indicates that said artificial extracellular matrix decreases cell migration.

23. The method of claim 22 further comprising:

providing a plurality of cells positioned between said first extracellular matrix and said second extracellular matrix of said in vivo model;

determining another rate of first migration of said plurality of cells from between said first extracellular matrix and said second extracellular matrix into said second extracellular matrix in said in vivo model; and determining another rate of second migration of said plurality of cells from between said first extracellular matrix and said second extracellular matrix into said second extracellular matrix, wherein an increase from the another rate of first migration to the another rate of second migration indicates that the artificial extracellular matrix increases cell migration, and wherein a decrease from the another rate of first migration to the another rate of second migration indicates that the artificial extracellular matrix decreases cell migration in said in vivo model.

* * * * *